United States Patent
Herzka et al.

(10) Patent No.: US 10,371,779 B2
(45) Date of Patent: Aug. 6, 2019

(54) APPARATUS AND METHOD FOR MAGNETIC RESONANCE IMAGING WITH HIGH SPATIAL TEMPORAL RESOLUTIONS

(75) Inventors: Daniel Alfredo Herzka, Rockville, MD (US); John Andrew Derbyshire, Silver Spring, MD (US)

(73) Assignee: The Johns Hopkins University, Baltimore, MD (US)

( * ) Notice: Subject to any disclaimer, the term of this patent is extended or adjusted under 35 U.S.C. 154(b) by 2462 days.

(21) Appl. No.: 14/889,135

(22) PCT Filed: Mar. 9, 2010

(86) PCT No.: PCT/US2010/026666
§ 371 (c)(1),
(2), (4) Date: Nov. 4, 2015

(87) PCT Pub. No.: WO2010/104855
PCT Pub. Date: Sep. 16, 2010

(65) Prior Publication Data
US 2016/0169999 A1 Jun. 16, 2016

Related U.S. Application Data

(60) Provisional application No. 61/158,503, filed on Mar. 9, 2009.

(51) Int. Cl.
*G01R 33/563* (2006.01)
*A61B 5/055* (2006.01)
(Continued)

(52) U.S. Cl.
CPC .......... *G01R 33/563* (2013.01); *A61B 5/0205* (2013.01); *A61B 5/0402* (2013.01);
(Continued)

(58) Field of Classification Search
None
See application file for complete search history.

(56) References Cited

U.S. PATENT DOCUMENTS

| | | | |
|---|---|---|---|
| 6,246,238 B1 | 6/2001 | Hennig | |
| 2004/0150402 A1* | 8/2004 | Sakakura | G01R 33/385 324/318 |

(Continued)

FOREIGN PATENT DOCUMENTS

JP 2004-526491 A 9/2004

OTHER PUBLICATIONS

International Search Report and Written Opinion issued in International Application No. PCT/US2010/026666 dated Sep. 29, 2010.
(Continued)

*Primary Examiner* — Jason T Yen
(74) *Attorney, Agent, or Firm* — Venable LLP; Henry J. Daley

(57) ABSTRACT

A magnetic resonance imaging (MRI) system, comprising a magnetic resonance imaging scanner. The MR scanner comprises a main magnet providing a substantially uniform main magnetic field B0 for a subject under observation, the subject represented by a spatial distribution of magnetizations; a radio frequency (RF) coil system configured to irradiate a plurality of radio frequency (RF) pulses into a region of interest of the subject and to detect a plurality of RF response signals emitted from the region of interest; a gradient coil system configured to provide a perturbation of the main magnetic field B0 using a gradient pulse sequence that causes the RF response signals to encode the spatial distribution of magnetizations in a Fourier domain on a plurality of read-out paths; and a controller in communication with the RF coil system and the gradient coil system to synchronously provide the RF coil system with the plurality of RF pulses and the gradient coil system with the gradient
(Continued)

pulse sequence. The gradient pulse sequence comprises a navigator pulse that causes one of the plurality of RF response signals to encode the spatial distribution of magnetizations in the Fourier domain on a pre-determined navigator path that represents a fixed projection of the region of interest of the subject, the pre-determined navigator path is suitable to be in a direction different from directions of the read-out paths, and the fixed projection of the subject is capable of tracking a motion of the subject.

8 Claims, 15 Drawing Sheets

(51) Int. Cl.
| | |
|---|---|
| A61B 5/00 | (2006.01) |
| G01R 33/48 | (2006.01) |
| G01R 33/567 | (2006.01) |
| A61B 5/0205 | (2006.01) |
| A61B 5/0402 | (2006.01) |
| A61B 18/20 | (2006.01) |
| G01R 33/36 | (2006.01) |
| G01R 33/385 | (2006.01) |
| A61B 5/08 | (2006.01) |
| A61B 5/11 | (2006.01) |
| A61B 5/113 | (2006.01) |
| A61B 18/00 | (2006.01) |

(52) U.S. Cl.
CPC ............ *A61B 5/055* (2013.01); *A61B 5/4836* (2013.01); *A61B 5/7207* (2013.01); *A61B 5/7257* (2013.01); *A61B 5/7285* (2013.01); *A61B 18/20* (2013.01); *G01R 33/36* (2013.01); *G01R 33/385* (2013.01); *G01R 33/4808* (2013.01); *G01R 33/4824* (2013.01); *G01R 33/5676* (2013.01); *G01R 33/56308* (2013.01); *G01R 33/56325* (2013.01); *A61B 5/08* (2013.01); *A61B 5/1102* (2013.01); *A61B 5/113* (2013.01); *A61B 2018/00577* (2013.01); *A61B 2018/00994* (2013.01); *A61B 2576/00* (2013.01)

(56) References Cited

U.S. PATENT DOCUMENTS

| 2004/0267111 | A1 | 12/2004 | Feinberg | |
|---|---|---|---|---|
| 2006/0224062 | A1* | 10/2006 | Aggarwal | G01R 33/5673 600/413 |
| 2007/0016000 | A1* | 1/2007 | Prince | A61B 5/055 600/410 |
| 2009/0030302 | A1* | 1/2009 | Taniguchi | A61B 6/5241 600/410 |

OTHER PUBLICATIONS

Buehrer et al., Prospective self-gating for simultaneous compensation of cardiac and respiratory motion. Magn Reson Med 2008;60(3):683-690.
Crowe et al., Automated rectilinear self-gated cardiac cine imaging. Magn Reson Med 2004;52(4):782-788.
Dixon, T Simple Proton Spectroscopic Imaging, Radiology 1984;153:189-194.
Fu et al., Orbital navigator echoes for motion measurements in magnetic resonance imaging. Magn Reson Med 1995;34(5):746-753.
Hiba et al., Cardiac and respiratory double self-gated cine MRI in the mouse at 7 T. Magn Reson Med 2006;55(3):506-513.
Hiba et al., Cardiac and respiratory self-gated cine MRI in the mouse: comparison between radial and rectilinear techniques at 7T. Magn Reson Med 2007;58(4):745-753.
Kellman et al., Fully automatic, retrospective enhancement of real-time acquired cardiac cine MR images using image-based navigators and respiratory motion-corrected averaging. Magn Reson Med 2008;59(4):771-778.
Lai et al., A dual-projection respiratory self-gating technique for whole-heart coronary MRA. J Magn Reson Imaging 2008;28(3):612-620.
Lai et al., Respiratory self-gated four-dimensional coronary MR angiography: a feasibility study. Magn Reson Med 2008;59(6):1378-1385.
Larson et al., Preliminary investigation of respiratory self-gating for free-breathing segmented cine MRI. Magn Reson Med 2005;53(1):159-168.
Larson et al., Self-gated cardiac cine MRI. Magn Reson Med 2004;51(1):93-102.
Leung et al., Free-breathing cine MRI. Magn Reson Med 2008;60(3):709-717).
Pipe JG. Motion correction with Propeller MRI: application to head motion and free-breathing cardiac imaging. Magn Reson Med 1999;42(5):963-969.
Stehning et al., Free-breathing whole-heart coronary MRA with 3D radial SSFP and self-navigated image reconstruction. Magn Reson Med 2005;54(2):476-480.
Welch et al., Spherical navigator echoes for full 3D rigid body motion measurement in MRI. Magn Reson Med 2002;47(1):32-41.
White et al., Electrocardiograph-independent, "wireless" cardiovascular cine MR imaging. J Magn Reson Imaging 1991;1(3):347-355.
Wyatt et al., Spherical Navigator Registration Using Harmonic Analysis for Prospective Motion Correction. 2005. Springer-Verlag. p. 738-749.

* cited by examiner

APPARATUS AND METHOD FOR MAGNETIC RESONANCE IMAGING WITH HIGH SPATIAL TEMPORAL RESOLUTIONS

CROSS-REFERENCE OF RELATED APPLICATION

This is a national stage application under 35 U.S.C. § 371 of PCT/US2010/026666 filed Mar. 9, 2010, the entire contents of which are incorporated herein by reference and this application claims priority to provisional U.S. Provisional Application No. 61/158,503 filed Mar. 9, 2009, the entire contents of which are hereby incorporated by reference.

BACKGROUND

1. Field of Invention

The current invention relates to magnetic resonance imaging systems, and more particularly to magnetic resonance imaging systems that provide reconstructed images of non-stationary organs.

2. Discussion of Related Art

Magnetic resonance imaging (MRI) is a reconstructive imaging technology that requires an exposure time, during which a subject's motion can pose a problem. For cardiac imaging, in particular, motion compensation is critical to obtaining high-quality, high-resolution diagnostic images.

Two different types of motion need to be compensated for during MR imaging of the heart, lung, liver, kidney, or other abdominal and thoracic organs. One is the respiratory motion and the other is the cardiac motion itself.

Respiratory motions in short scans may be removed by asking the subject under observation to engage in breath-holds for the duration of the scan. However, this limits the maximum duration of the scan, which in turn limits the achievable image quality as well as spatial and temporal resolutions of the image. However, high-resolution and high-quality images require longer scan times, making short scans non-feasible. Furthermore, certain patient populations, such as, for example, patients with heart failure, cardiac hypertrophy, or other cardiac conditions, can only hold their breath for a very short period of time or they cannot hold their breath at all. In these patients, breath-hold studies are very difficult, if not impossible. Most commercial scanners are equipped with respiratory bellows, which measure the general distention of chest cavity during breathing. However, these bellows are unreliable as they do not necessarily represent the true motion due to breathing and therefore their use is limited to simple patient monitoring and not for gating of imaging acquisition.

In free-breathing scans, conventional motion compensation techniques use respiratory navigator pulses that monitor a secondary site as an index of the respiratory motion. The secondary site may be, for example, the lung-liver interface on the right side of the body (also known as the right hemidiaphragm). Navigator pulses typically acquires a pencil beam 1D image that spans the lung-liver interface, producing a signal that can be monitored over time for each heart beat. The signal can be used to estimate motion in the foot-head direction. Navigator pulses can be used to accept or reject data based on the position of the organ of interest, or to correct acquired data to partially compensate for motion. Respiratory navigator pulses are generally effective, but can be difficult to prescribe on all patients. They are also difficult to implement on patients with variable respiratory patterns. Furthermore, and on a more fundamental level, these diaphragmatic navigator pulses attempt to estimate the motion of, for example, the heart, from the motion of another organ (the liver-lung interface), leading to errors. These navigator pulses assume the only relevant motion axis due to breathing is the foot-head direction and typically use fixed scaling to correct for cardiac motion, for example, for every 1 cm of liver motion, there may be an estimated 0.6 cm of motion at the base of the heart. These navigator pulses are also known to be limited in the sharpness of images because the resolution of the motion detectable with navigator pulses is maxed out for resolutions below approximately 0.75 mm. Finally, these respiratory navigator pulses are not in the same pulse sequence as the imaging pulse sequence for imaging the organ of interest. A separate pulse sequence is most useful for single-phase imaging, for example, diastolic imaging or coronary imaging, but is limited to non-steady-state acquisition and may not be useful in, for example, functional studies due to the interruption and disturbance of the steady state.

Typically, cardiac motion is compensated for by synchronizing the acquisition to an ECG waveform that is obtained by placing electrodes on the patient's chest. High-resolution imaging is achieved by combining MR imaging data acquired during corresponding portions of multiple cardiac cycles. This is a generally robust and widespread solution, and all MR system manufacturers have built-in ECG gating devices. However, ECG gating can fail for several reasons. First, at the high fields of the new clinical scanners (for example, those at 3.0 T or above) the ECG signal can become less reliable due to distortion of the ECG waveform by the magnetohydrodynamic effect. Second, and more importantly, ECG gating can lead to low quality images when the assumption of a periodic heartbeat breaks down. Cardiac MR images are normally acquired over several heartbeats, a process referred to as segmentation. All data is combined assuming that each heartbeat is identical to the previous one. For example, patients with cardiac arrhythmias (e.g. premature ventricular contractions) can have irregular heartbeats periodically, corrupting the acquired data and introducing artifacts into the MR images. It is known that a significant fraction of the population have high heart rate variability, that is, their heartbeat length varies a lot, even during a short period of time, which makes the assumption that all heartbeats are the same less true.

Recently, the concept of self navigation in which the raw magnetic resonance (MR) imaging data itself is used to identify, measure, and compensate for motion have emerged. Self-navigation may remove the need for external sensing devices to monitor both cardiac and respiratory motion. With self-navigation, the patient need not be disturbed to perform breath-holds (which is best for the sickest of patients who may be the ones most in need of an MR examination). The most basic self-navigation techniques attempt to estimate the underlying respiratory patterns, but more advanced and more recent techniques also extract the cardiac motion from the raw MR data itself.

Currently available self navigation techniques acquire low-spatial resolution data at high temporal resolution: every time image data is collected (also known as the repetition time of TR). Other navigator techniques acquire higher spatial resolution data every cardiac phase, sacrificing temporal resolution. All currently available methods have a net loss in efficiency, that is, either TR is extended to include the acquisition of the navigator data (reducing the fraction of time spent acquiring image data) or they extend the scan time, by taking complete TRs to acquire non-phase encoded data.

There are already several implementations of self-navigation techniques seen in the literature. A basic technique involves the acquisition of images in real-time (very fast) and using the images to determine the underlying motion of the heart (Kellman P, Chefd'hotel C, Lorenz C H, Mancini C, Arai A E, McVeigh E R. Fully automatic, retrospective enhancement of real-time acquired cardiac cine MR images using image-based navigators and respiratory motion-corrected averaging. Magn Reson Med 2008; 59(4):771-778; Pipe J G. Motion correction with PROPELLER MRI: application to head motion and free-breathing cardiac imaging. Magn Reson Med 1999; 42(5):963-969; Leung A O, Paterson I, Thompson R B. Free-breathing cine MRI. Magn Reson Med 2008; 60(3):709-717). These techniques are generally limited by the amount of time it takes to acquire a complete image though they are able to resolve more complicated motion patterns.

Other self-navigation techniques that derive motion patterns from the raw data itself include techniques that use a multiple projections for images and techniques that use a single projection acquired repeatedly. For the latter category, the projection can be acquired sporadically (e.g., every cardiac phase with relatively low temporal resolution) every time imaging data is acquired. This approach incurs an extra cost of time in the TR (e.g. a free-induction-decay, or FID, signal is read-out at the beginning of the TR or an extra echo at the end of the TR) even when performed with very low resolution (Leung A O, Paterson I, Thompson R B. Free-breathing cine MRI. Magn Reson Med 2008; 60(3):709-717; White R D, Paschal C B, Clampitt M E, Spraggins T A, Lenz G W. Electrocardiograph-independent, "wireless" cardiovascular cine MR imaging. J Magn Reson Imaging 1991; 1(3):347-355; Wyatt C A, N; Kraft. R. Spherical Navigator Registration Using Harmonic Analysis for Prospective Motion Correction. 2005. Springer-Verlag. p 738-749; Fu Z W, Wang Y, Grimm R C, Rossman P J, Felmlee J P, Riederer S J, Ehman R L. Orbital navigator echoes for motion measurements in magnetic resonance imaging. Magn Reson Med 1995; 34(5):746-753; Welch E B, Manduca A, Grimm R C, Ward H A, Jack C R, Jr. Spherical navigator echoes for full 3D rigid body motion measurement in MRI. Magn Reson Med 2002; 47(1):32-41; Hiba B, Richard N, Janier M, Croisille P. Cardiac and respiratory double self-gated cine MRI in the mouse at 7 T. Magn Reson Med 2006; 55(3): 506-513; Larson A C, White R D, Laub G, McVeigh E R, Li D, Simonetti O P. Self-gated cardiac cine MRI. Magn Reson Med 2004; 51(1):93-102; Crowe M E, Larson A C, Zhang Q, Carr J, White R D, Li D, Simonetti O P. Automated rectilinear self-gated cardiac cine imaging. Magn Reson Med 2004; 52(4):782-788; Larson A C, Kellman P, Arai A, Hirsch G A, McVeigh E, Li D, Simonetti O P. Preliminary investigation of respiratory self-gating for free-breathing segmented cine MRI. Magn Reson Med 2005; 53(1):159-168; Hiba B, Richard N, Thibault H, Janier M. Cardiac and respiratory self-gated cine MRI in the mouse: comparison between radial and rectilinear techniques at 7 T. Magn Reson Med 2007; 58(4):745-753; Lai P, Larson A C, Bi X, Jerecic R, Li D. A dual-projection respiratory self-gating technique for whole-heart coronary MRA. J Magn Reson Imaging 2008; 28(3):612-620; Buehrer M, Curcic J, Boesiger P, Kozerke S. Prospective self-gating for simultaneous compensation of cardiac and respiratory motion. Magn Reson Med 2008; 60(3):683-690; Lai P, Larson A C, Park J, Can J C, Li D. Respiratory self-gated four-dimensional coronary MR angiography: a feasibility study. Magn Reson Med 2008; 59(6):1378-1385; Stehning C, Bornert P, Nehrke K, Eggers H, Stuber M. Free-breathing whole-heart coronary MRA with 3D radial SSFP and self-navigated image reconstruction. Magn Reson Med 2005; 54(2):476-480).

Thus, there is a need for an improved magnetic resonance imaging system for use with non-stationary organs.

SUMMARY

Some embodiments of the current invention provide a magnetic resonance imaging (MRI) system, comprising a magnetic resonance imaging scanner. The MR scanner comprises a main magnet providing a substantially uniform main magnetic field $B_0$ for a subject under observation, the subject represented by a spatial distribution of magnetizations; a radio frequency (RF) coil system configured to irradiate a plurality of radio frequency (RF) pulses into a region of interest of the subject and to detect a plurality of RF response signals emitted from the region of interest; a gradient coil system configured to provide a perturbation of the main magnetic field $B_0$ using a gradient pulse sequence that causes the RF response signals to encode the spatial distribution of magnetizations in a Fourier domain on a plurality of read-out paths; and a controller in communication with the RF coil system and the gradient coil system to synchronously provide the RF coil system with the plurality of RF pulses and the gradient coil system with the gradient pulse sequence. The gradient pulse sequence comprises a navigator pulse that causes one of the plurality of RF response signals to encode the spatial distribution of magnetizations in the Fourier domain on a pre-determined navigator path that represents a fixed projection of the region of interest of the subject, the pre-determined navigator path is in a direction different from directions of the read-out paths, and the fixed projection of the subject is capable of tracking a motion of the subject.

Some embodiments of the current invention provide a method for designing a gradient pulse sequence suitable for magnetic resonance imaging (MRI) of a subject under observation in a MRI system, the subject represented by a spatial distribution of magnetizations. The method comprises: generating a first gradient pulse waveform suitable to encode the spatial distribution of magnetizations on a first read-out path; generating a second gradient pulse waveform suitable to encode the spatial distribution of magnetizations on a second read-out path; and inserting a navigator gradient pulse suitable to encode the spatial distribution of magnetizations on a fixed navigator path that substantially connects an end point of the first read-out path with a starting point of the second read-out path. The fixed navigator path represents a projection of the subject under observation, and the projection of the subject is suitable for tracking a motion of the subject.

Some embodiments of the current invention provide a method for magnetic resonance imaging of a subject under observation. The subject is represented by a spatial distribution of magnetizations. The method comprises (a) placing the subject in a main magnet providing a substantially uniform magnetic field, (b) encoding, in a data matrix, the spatial distribution of magnetizations on a first read-out path in a Fourier domain; (c) encoding, in the data matrix, the spatial distribution of magnetizations on a first fixed navigator path in the Fourier domain that substantially connects an end point of the first read-out path with a starting point of a second read-out path; (d) encoding, in the data matrix, the spatial distribution of magnetization on the second read-out path in the Fourier domain; and (e) outputting the data matrix to a storage device, wherein a temporal duration from (b) to (d) corresponds to a repetition time (TR); the fixed navigator path represents a projection of the subject under observation, and the projection of the subject is suitable for tracking a motion of the subject.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
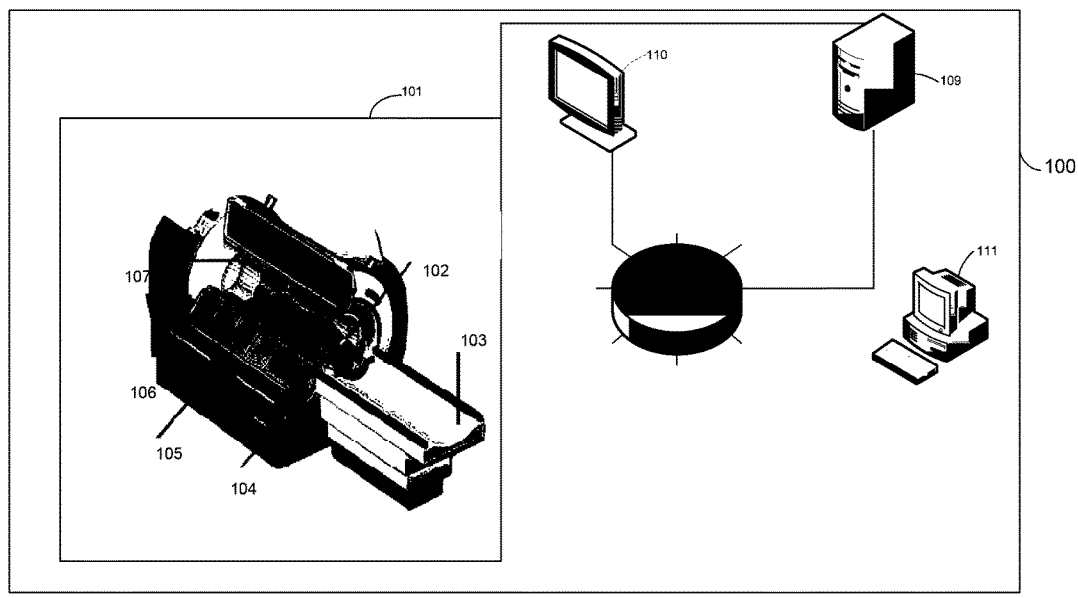
FIG. 1 is a schematic illustration of a magnetic resonance imaging (MRI) system according to some embodiments of the current invention.

FIG. 1 is a schematic illustration of a magnetic resonance imaging (MRI) system 100 according to an embodiment of the current invention.

The MRI system 100 includes a magnetic resonance scanner 101, capable of imaging a subject 102 under observation on scanner bed 103. Magnetic resonance scanner 101 is located on base 104 and has a main magnet 105, a gradient coil system 106, and a radio-frequency (RF) coil system 107. Main magnet 105 provides a substantially uniform main magnetic field $B_0$ for subject 102. Gradient system 106 provides a perturbation of the main magnetic field $B_0$ to encode spatial information of the constituent water molecules with a region of interest of subject 102 under observation. The spatial information may be a spatial distribution of magnetizations. Radio-frequency (RF) coil system 107 transmits RF pulses into a region of interest of subject 102 under observation and receives magnetic resonance (MR) response signals from subject 102.

The gradient coil system 106 may use a gradient pulse sequence that causes the RF response signals to encode the spatial distribution of magnetizations in a Fourier domain on a plurality of read-out paths. The gradient pulse sequence comprises a navigator pulse that causes one of said plurality of RF response signals to encode the spatial distribution of magnetizations in the Fourier domain on a pre-determined navigator path that represents a fixed projection of a region of interest of the subject 102. The pre-determined navigator path is in a direction different from the directions of the read-out paths. The fixed projection of said subject is capable of tracking a motion of the subject 102. The motion may be one of a cardiac motion or a respiratory motion. The region of interest may be a heart, a lung, a liver, a kidney, or other organs of interest in the thoracic or abdominal cavities.

RF coil system 107 comprises at least one radio frequency (RF) coil configured to irradiate a radio frequency (RF) pulse into a region of interest of the subject 108. The RF coil may be, for example, a surface coil, a neck coil, an extremity coil, a head coil, a body, a phased-array coil, etc. The RF coil may be embodied as a solenoid, a planar coil, a volume coil, a quadrature coil, or variations thereof. The RF coil may be for transmission only or for both transmission and reception. RF coil system 107 may further comprise a power amplifier to amplify the RF pulse being transmitted or the received magnetic resonance signals. The power amplifier may be programmed or configured to amplify at more than one level of amplification. RF coil system 107 may further comprise matching and/or tuning networks for impedance matching and/or frequency tuning purposes.

The MRI system 100 may further include a data storage unit 108 and a signal processing unit 109. Data storage unit 108 is in communication with signal processing unit 109 to store magnetic signals from the region of interest of subject 102 under observation. The subject may be, for example, a human, an animal, a phantom, a sample, or combinations thereof. The region of interest may be, for example, a brain, a heart, a muscle, a liver, a kidney, a knee, a neck, etc.

Data storage unit 108 may be, for example, a hard disk drive, a network area storage (NAS) device, a redundant array of independent disks (RAID), a flash drive, an optical disk, a magnetic tape, a magneto-optical disk, etc. However, the data storage unit 108 is not limited to these particular examples. It can include other existing or future developed data storage devices without departing from the scope of the current invention.

Signal processing unit 109 is in communication with magnetic resonance scanner 101 to receive magnetic resonance signals from the region of interest in response to the RF pulse. Signal processing unit 109 may be partially or totally incorporated within a structure housing magnetic resonance scanner 101. Signal processing unit 109 may be at least partially incorporated in a workstation that is structurally separate from and in communication with magnetic resonance scanner 101. Signal processing unit 109 may be incorporated in a workstation that is structurally separate from and in communication with magnetic resonance scanner 101. A workstation can be a computer having at least one central processing unit (CPU) and one memory, for example, static random access memory (SRAM), dynamic random access memory (DRAM), erasable programmable random access memory (EPROM), non-volatile Flash memory, etc.

Signal processing unit 109 may reconstruct a plurality of images of the region of interest of the subject 108 based on the received RF response signals. Signal processing unit 109 may further combine at least two of the plurality of reconstructed images by a root-sum-square process. Signal processing unit 109 may combine the received RF response signals alternately and may combine the received RF response signals using at least one complex summation.

The output from signal processing unit 109 may be visualized on a display device, such as, for example, viewing station 110 or a console station 111. Viewing station 110 or console station 111 may be, for example, a cathode ray tube (CRT) monitor, a liquid crystal display (LCD) monitor, a digital light projection (DLP) monitor, a plasma screen, an organic light emitting diode (OLED), etc. The processed results may be used for further analysis and diagnosis.

The MRI system 100 may further comprise a monitoring device to monitor the motion of subject 102 under observation. The monitoring device may be, for example, a electrocardiogram (ECG) device, a respiration gating device, etc. The MRI system 100 may also comprise, an intervention device to provide treatment to said region of interest. The intervention device may be, for example, a RF ablator, an ultrasound applicator, a laser ablator, a laparoscopic device, etc.

Figure 2:
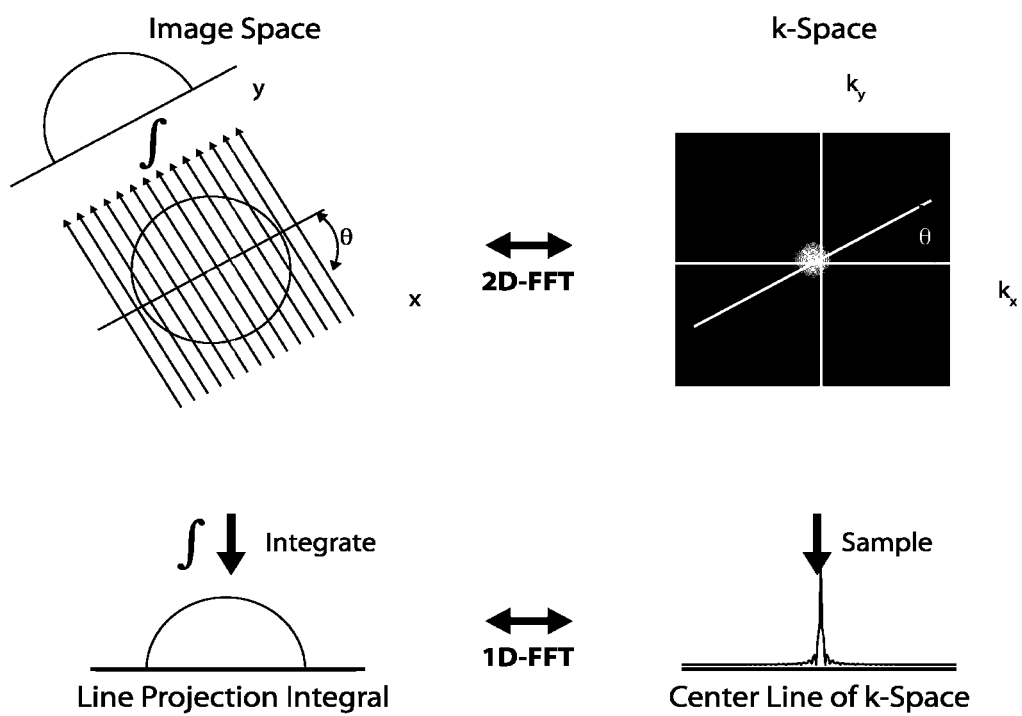
FIG. 2 is an illustration of the correspondence between the image space and the k-space, as well as the correspondence between a line projection integral of the image space and a center line of k-space, according to some embodiments of the current invention.

FIG. 2 is an illustration of the correspondence between the image space and the k-space, as well as the correspondence between a line projection integral of the image space and a center line of k-space, according to some embodiments of the current invention MR imaging is a reconstructive technology that obtains raw imaging data (for example, RF response signals from subject 102) in a Fourier domain (also known as k-space) and reconstruct an image representing the subject 102 using a transformation from the Fourier domain to image space.

The central slice theorem is at the center of self-navigation in MR. The central slice theorem states that 1D Fourier Transform of the projection of the image in any particular direction (at angle θ+90° in this example) is equal to the line in k-space which crosses the center of k-space at the same angle. Hence, when a line of k-space that crosses the center is recorded, as is typically during imaging, that line corresponds to the projection of the complete image onto a line. That line possesses a lot of information pertaining of the motion of the tissue being imaged, and can therefore be used to accept or reject data based on motion, as well as to correct data based on the measured tissue motion.

The central slice theorem can also be extended into a 3-dimensional setting. The 1D Fourier Transform of the projection of a volume onto a line at any angle in 3D-space is equal to the line of k-space that crosses the center of k-space at the same angle in 3d-space. Hence, when doing more time-consuming 3D imaging, single line projections still contain a lot of information pertaining to the motion being imaged.

Figure 3:
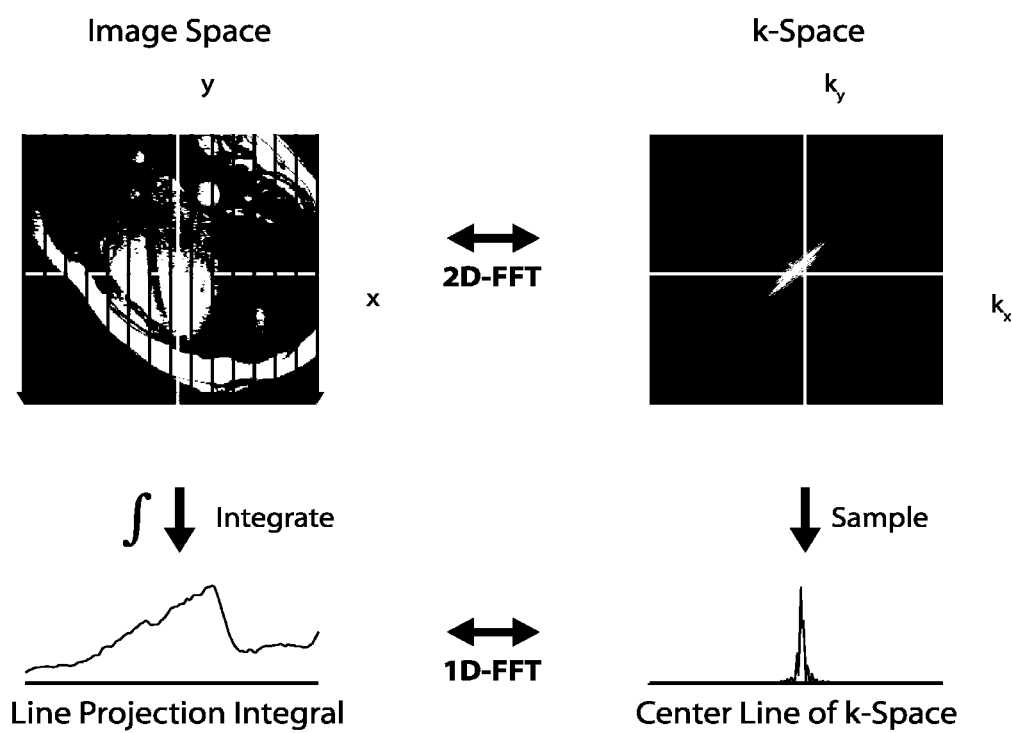
FIG. 3 is another illustration of the correspondence between the image space and the k-space, as well as the correspondence between a line projection integral of the image space and a center line of k-space, according to some embodiments of the current invention.

FIG. 3 is another illustration of the correspondence between the image space and the k-space, as well as the correspondence between a line projection integral of the image space and a center line of the k-space, according to some embodiments of the current invention. In this example, a cardiac MR image is shown, along with its Fourier transforms.

A high signal to noise ratio (SNR) imaging sequence, for example, a balanced steady-state free precession (SSFP) imaging sequence, may be used to obtain a high spatial and temporal resolution navigator projection in an efficient manner with unconstrained projection directions (angle θ). SSFP sequence is fast with TRs<6 ms, and efficient in that it samples data for a large fraction of every repetition time (TR). Furthermore, the magnetization is recycled from one TR to the next so that the intrinsic SNR of each such data acquisition is independent of TR. However, SSFP suffers from "banding" and other artifacts if TR is extended too much (for example, beyond 6 ms for cardiac imaging on a 1.5 T MRI system, for other organs or on other systems, the bound for TR may be different). Previously, due to MR system hardware limitations, it has been difficult to acquire multiple lines of k-space and/or navigator projections without extending TR beyond 6 ms. The availability of faster gradient hardware (with higher maximum slew rates) and new, more efficient pulse sequence gradient waveform design (e.g., HOT, EPI, FLASH pulse implementations) now permit multiple echoes and multiple navigator projections to be acquired in a single TR. However, neither efficient waveforms nor faster hardware is required for this invention. In fact, some embodiments of the current invention may use other imaging pulse sequences, for example, echo-planar imaging (EPI), fast low angle shot (FLASH), gradient recalled spoiled gradient echo (SPGR), fast spin echo (FSE), etc.

Figure 4A:
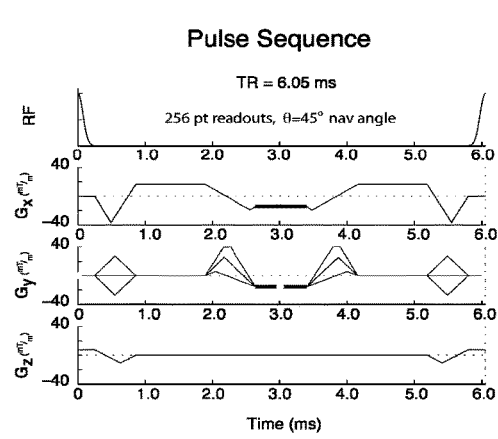
FIG. 4A shows a pulse sequence with a navigator gradient pulse waveform according to an embodiment of the current invention.
Figure 4B:
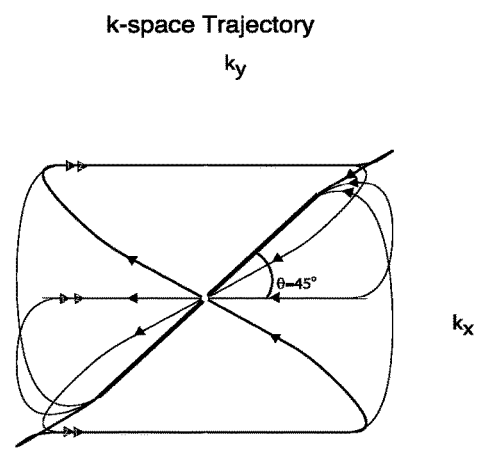
FIG. 4B shows the corresponding k-space trajectory of the pulse sequence show in FIG. 4A according to an embodiment of the current invention.

FIG. 4A shows a dual-echo SSFP sequence pulse sequence with a navigator gradient pulse waveform according to an embodiment of the current invention. FIG. 4B shows the corresponding k-space trajectory of the dual-echo SSFP sequence pulse sequence show in FIG. 4A according to an embodiment of the current invention.

This example in FIGS. 4A and 4B shows two read-out paths and a single constant navigator path (nread=2, nproj=1) per repetition time (TR). The constant navigator path corresponds to a single predetermined projection of the image space. In this example, the navigator projection angle θ is 45°, and full k-space is sampled for both readout echoes. The k-space trajectories for three phase encode (PE) steps (max PE=blue, no PE=black, min PE=red) are shown in FIG. 4B. TR in this example is relatively long due to the long transitions, in particular, for the min PE (red), which requires that k-space be traversed from the end of the first readout (bottom right) to the beginning of the navigator projection (top right). The navigator projection (thick black line) is constant regardless of phase encode step, making it possible to detect motion by monitoring a structure over time. The yellow dot highlights time points at which the center of k-space is crossed (start, middle of navigator echo, end). Transparent arrowheads denote portions of the trajectory that are not in the kx-ky plane due to slice selection.

Figure 5A:
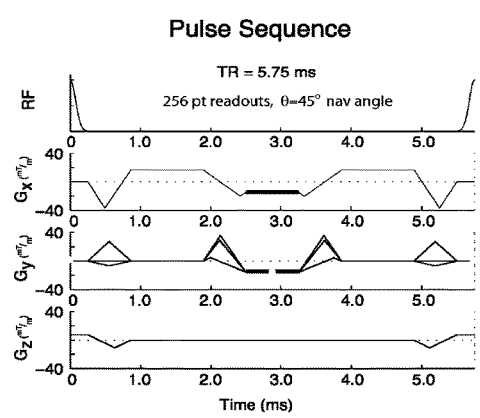
FIG. 5A shows another pulse sequence with a navigator gradient pulse waveform according to an embodiment of the current invention.
Figure 5B:
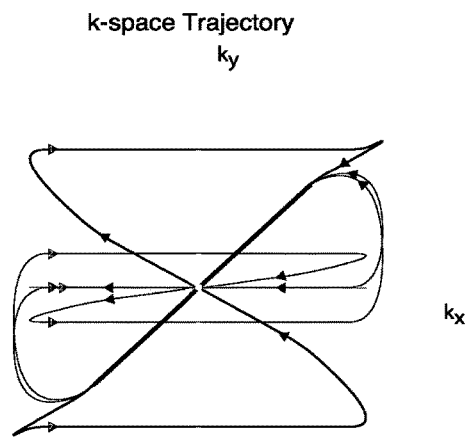
FIG. 5B shows the corresponding k-space trajectory of the pulse sequence show in FIG. 5A according to an embodiment of the current invention.

FIG. 5A shows another dual-echo SSFP sequence with a navigator gradient pulse waveform according to an embodiment of the current invention. FIG. 5B shows the corresponding k-space trajectory of the dual-echo SSFP pulse sequence shown in FIG. 5A according to an embodiment of the current invention.

This example in FIGS. 5A and 5B utilizes a Partial Fourier Factor (PFF) of ⅝. Relative to the previous example, this instance of the pulse sequence has a shorter TR (5.75 ms) due to reduced displacements in k-space (curved portions of min PE trajectory in red). In this example, only a PFF of k-space is acquired (⅝ in this example). The use of a Partial Fourier Factor (PFF) reduces the transition from a first read-out path to a second read-out path, thus shortening the minimum TR achievable. Again, the navigator projection remains constant throughout all PEs. For this design, minimum TR is found for a navigator projection angle of ~15°.

Figure 6:
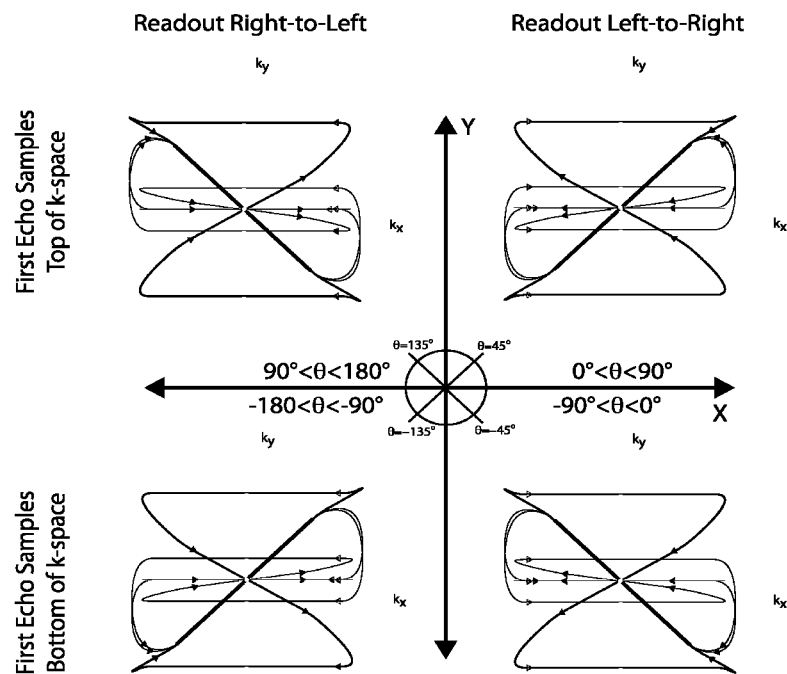
FIG. 6 shows the read-out path directions, depending on the direction of the navigator path, according to some embodiments of the current invention.

FIG. 6 shows the read-out path directions, depending on the direction of the navigator path, according to some embodiments of the current invention. A first optimization uses different trajectories to minimize TR, depending on the projection angle of the navigator path in k-space. For example, if the desired navigator projection angle θ is between −90 and 90 degrees, then read-out paths should be from left to right. Similarly, if θ>90° or θ<−90°, then the read-out path should be right to left. A second optimization is related to the fraction of k-space sampled by the each echo. For positive θ, it is best if the first echo samples the top fraction of k-space. If θ is negative, the shortest TR is achieved if the first echo samples the bottom fraction of k-space. The minimization in TR is achieved by reducing the length of transition (curved portions of the trajectories). As an illustrating example, if −90°<θ<0°, and the first echo samples the top half of k-space, then at the end of the first echo, a large jump in k-space (from the top right corner to the beginning of the navigator projection in the bottom right corner) would be required, thus extending TR.

Figure 7:
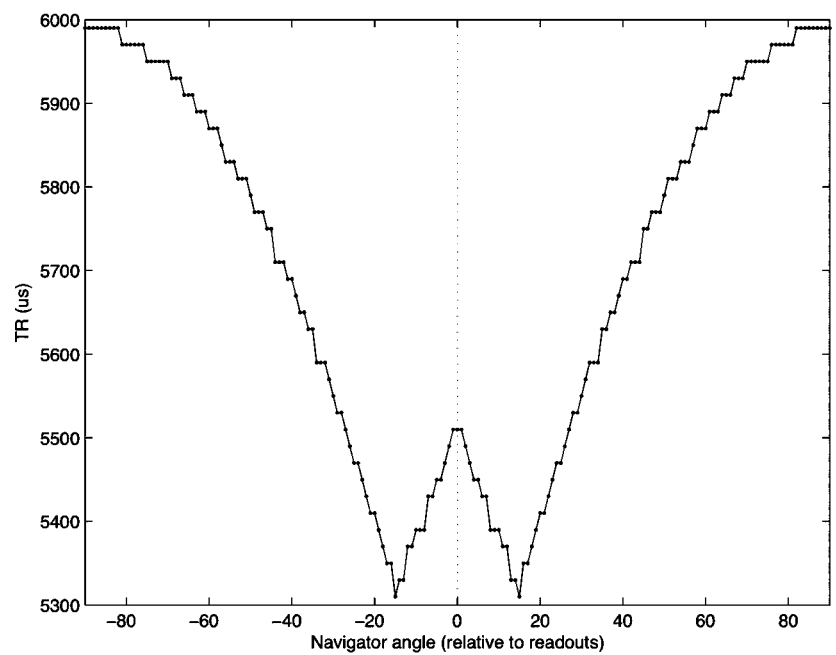
FIG. 7 shows repetition time (TR) as a function of the angle of the navigator path in the k-space, according to some embodiments of the current invention.

FIG. 7 shows repetition time (TR) as a function of the angle of the navigator path in the k-space, according to some embodiments of the current invention. When navigator path angles drop below 0°, the fraction of k-space sampled for each echo is switched. The minimum TR can be found at around 16°. The simulation used 256 pt readouts, 192 pt single navigator paths, and a PFF of ⅝. In this simulation, the directions of readout and the polarity of the first echo are already optimized according to FIG. 6.

Figure 8:
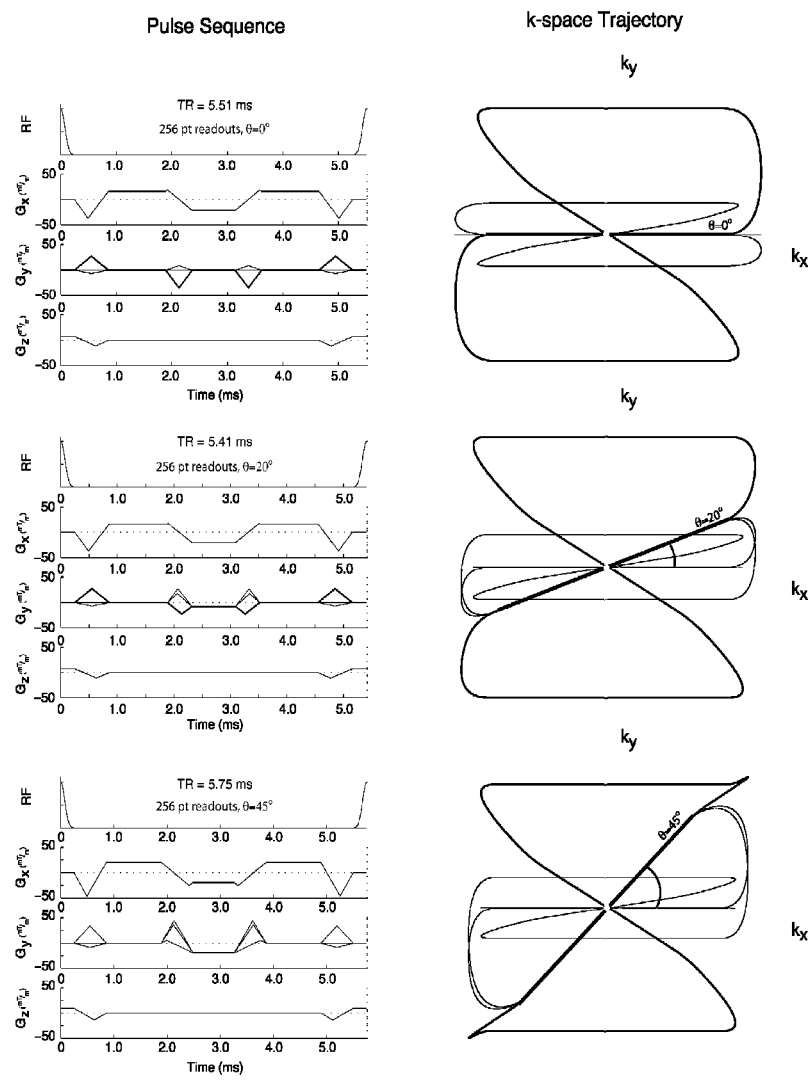
FIG. 8 shows three pulse sequences with different TRs and the corresponding k-space trajectories for the three respective navigator paths at different angles according to an embodiment of the current invention.

FIG. 8 shows three pulse sequences with different TRs and the corresponding k-space trajectories for the three respective navigator paths at different angles according to an embodiment of the current invention. In this example, TR varies with navigator projection angle and a PFF of ⅝ is used (Blue=max PE, Black=no PE, Red=min PE).

Figure 9A:
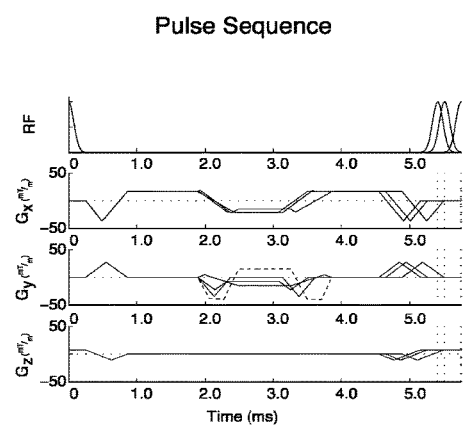
FIG. 9A shows a pulse sequence with four navigator pulses according to an embodiment of the current invention.
Figure 9B:
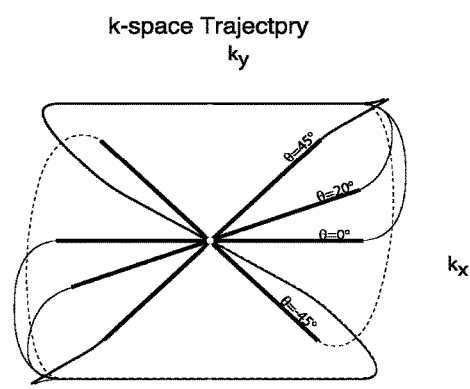
FIG. 9B shows the superimposed k-space trajectories corresponding to the pulse sequence in FIG. 9A according to an embodiment of the current invention.

FIG. 9A shows a pulse sequence with four navigator pulses according to an embodiment of the current invention. FIG. 9B shows the superimposed k-space trajectories corresponding to the pulse sequence in FIG. 9A according to an embodiment of the current invention. In this example, if θ=−45° and the fraction of k-space sampled is not changed, then TR is greatly extended since there are large transitions in k-space (long curved dotted lines).

The pulse sequences discussed above can be extended to acquire multiple navigator projections in a single TR. For example, acquiring two perpendicular projections would allow monitoring of motion along two directions in high resolution. As will be discussed below, sequences can have $N_{read}=2$ and $N_{proj}=2$. To keep TR sufficiently short to avoid off-resonance artifacts (e.g. SSFP banding), it may be necessary to reduce the readout resolution for these sequences.

Figures 10A, 10B:
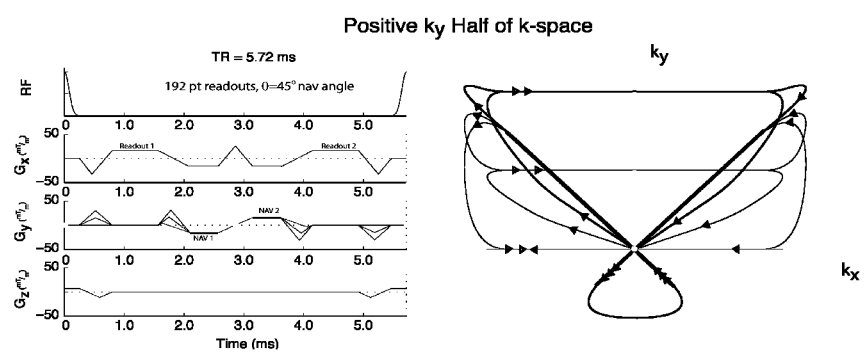
FIG. 10A shows a pulse sequence with two navigator pulses when the positive half of $k_y$ is traversed according to an embodiment of the current invention.
FIG. 10B shows the k-space trajectory corresponding to the pulse sequence in FIG. 10A according to an embodiment of the current invention.
Figures 10C, 10D:
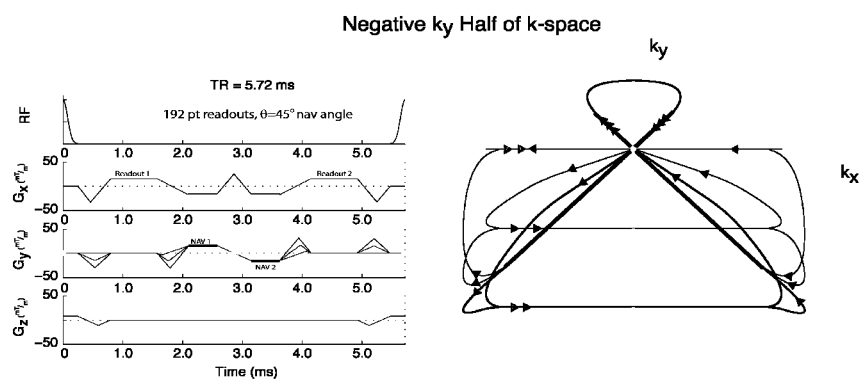
FIG. 10C shows the same pulse sequence as in FIG. 10A with two navigator pulses when the negative half of $k_y$ is traversed according to an embodiment of the current invention.
FIG. 10D shows the k-space trajectory corresponding to the pulse sequence in FIG. 10C according to an embodiment of the current invention.

FIG. 10A shows a pulse sequence with two navigator pulses when the positive half of $k_y$ is traversed according to an embodiment of the current invention. FIG. 10B shows the k-space trajectory corresponding to the pulse sequence in FIG. 10A according to an embodiment of the current invention. FIG. 10C shows the same pulse sequence as in FIG. 10A with two navigator pulses when the negative half of $k_y$ is traversed according to an embodiment of the current invention. FIG. 10D shows the k-space trajectory corresponding to the pulse sequence in FIG. 10C according to an embodiment of the current invention.

In this example, two read-out echoes are acquired and Nproj=2, with θ=45°, 135°. According to this pulse sequence, the same line of k-space is acquired twice, though the phase differences between echo 1 and echo 2 make them conjugates of each other. The top half and bottom half are k-space areas that are each acquired with two different navigator projections. The conjugate symmetry of k-space makes the two navigator projections with the same angle comparable. Also, to minimize TR in this example, only ⅝ of each navigator projection is acquired. The two thick black lines in the k-space trajectories are the navigator projections that remain constant throughout all phase encode steps, the yellow dot represents the center of k-space, and the semi-transparent arrows on the different phase encoding trajectories denote moving towards or away from the center of k-space at the beginning or end of a TR. Three different representative phase encodes (PEs) are displayed in each diagram.

Figure 11A:
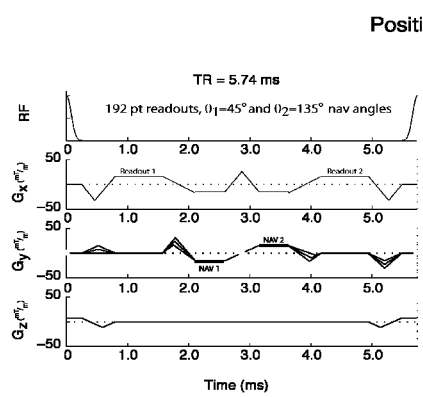
FIG. 11A shows another pulse sequence with two navigator pulses when the positive half of $k_y$ is traversed according to an embodiment of the current invention.
Figure 11B:
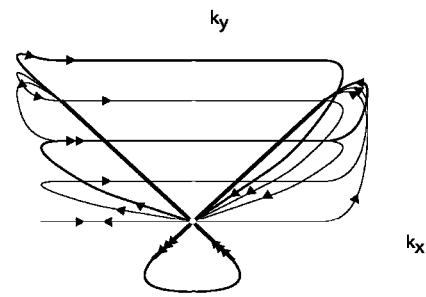
FIG. 11B shows the k-space trajectory corresponding to the pulse sequence in FIG. 11A according to an embodiment of the current invention.
Figure 11C:
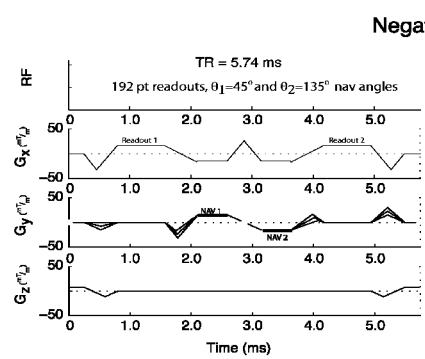
FIG. 11C shows the same pulse sequence as in FIG. 11A with two navigator pulses when the negative half of $k_y$ is traversed according to an embodiment of the current invention.
Figure 11D:
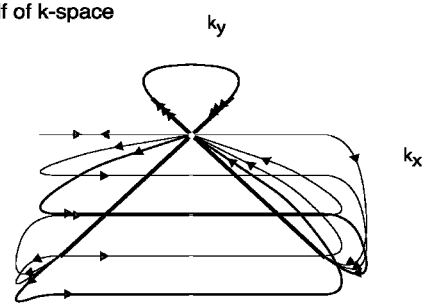
FIG. 11D shows the k-space trajectory corresponding to the pulse sequence in FIG. 11C according to an embodiment of the current invention.

FIG. 11A shows another pulse sequence with two navigator pulses when the positive half of $k_y$ is traversed according to an embodiment of the current invention. FIG. 11B shows the k-space trajectory corresponding to the pulse sequence in FIG. 11A according to an embodiment of the current invention. FIG. 11C shows the same pulse sequence as in FIG. 11A with two navigator pulses when the negative half of $k_y$ is traversed according to an embodiment of the current invention. FIG. 11D shows the k-space trajectory corresponding to the pulse sequence in FIG. 11C according to an embodiment of the current invention.

The pulse sequences in FIGS. 10 and 11 differ in the phase encode (PE) ordering scheme and in the possible processes for echo combination. In the example of FIG. 11, two read-out echoes (Nread=2) are acquired as well as two navigator projections (Nproj=2), with θ=45°, 135°. According to this pulse sequence, the different lines of k-space are acquired each TR, and the top and bottom half of k-space are acquired with navigators in opposite orientations. Again, the two thick black lines in the k-space trajectories are the navigator projections that remain constant throughout all phase encode steps, the yellow dots represent crossings of the center of k-space, and the semi-transparent arrows on the different phase encoding trajectories denote moving towards or away from the center of k-space at the beginning or end of a TR. Three different representative phase encodes are displayed in each diagram.

A central feature of pulse sequences discussed here according to some embodiments of the current invention is that at least two imaging read-out echoes are acquired in addition to the navigator projection(s). With SSFP imaging, echoes are typically acquired centered between RF pulses, with the TE point occurring exactly halfway and producing a spin echo, rather than a gradient recalled echo. With the sequence proposed here according to some embodiments of the current invention, the echoes are shifted relative to the original TE point, resulting in additional (and opposite) phase on the two imaging echoes. Hence, if combined directly into a single k-space, it is likely they will produce artifacts. Therefore, several methods for echo combination are possible, including, for example, (1) reconstructing a complete image with each echo (or an image acquired with a partial Fourier factor ranging from 0.5-1) and combining the two images via a root-sum-squares (RSS) process; (2) acquiring alternating echoes (e.g. evens for the first echo, odds for the second echo) and reconstruct the images using a process that creates images with ghosts via combination of the first and second read-out echoes in the base image, and removing the ghosts afterwards (requires a time series in which even/odd acquisitions alternate); and (3) acquiring the same read-out echo twice, and combining using a complex summation of the echoes (treating them as averaging). Because the imaging read-out echoes are complex conjugates in some embodiments of the current invention, in principle, they can be used to estimate off-resonance after coil phase correction (and probably would require stationary samples). Alternate methods of combining the imaging read-out echoes may be available without deviating from the true spirit of the current invention.

Figure 12:
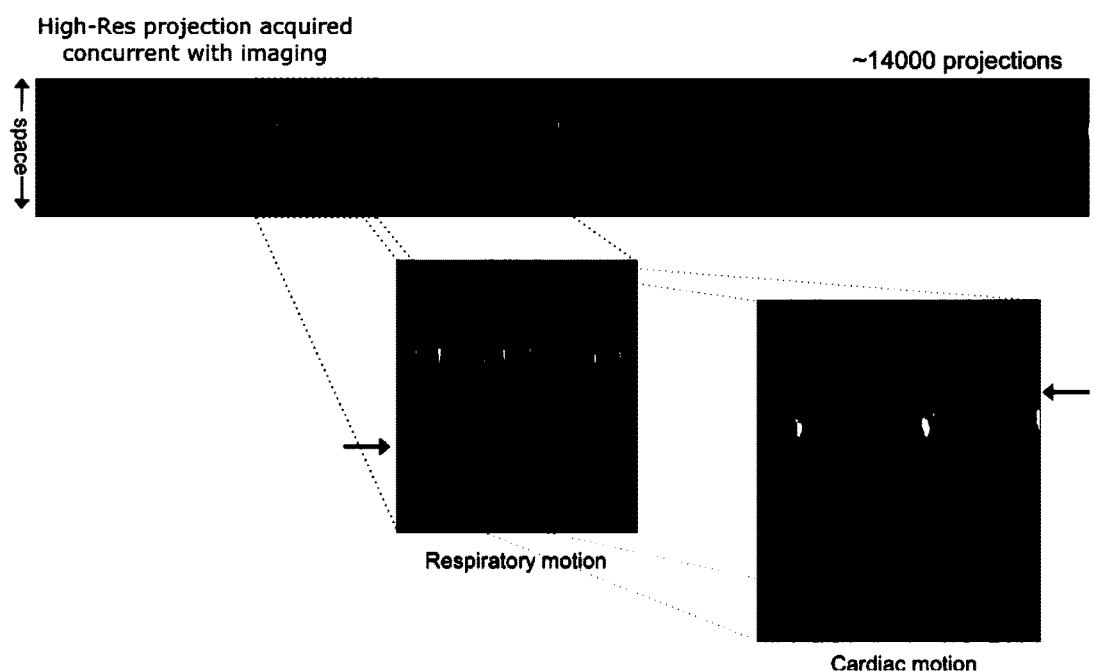
FIG. 12 shows experimental results of projection data obtained according to some embodiments of the current invention.

FIG. 12 shows experimental results of projection data obtained according to some embodiments of the current invention. This preliminary result was obtained with the pulse sequence shown in FIG. 5a. Navigator projection data were acquired over a 80-second scan. This result displays over 14000 projections acquired at a spatial resolution of 1.77 mm at a temporal rate every 5.7 ms (192 pt navigators, 256 pt readouts, 20°). The enlarged view of a subset of profiles spanning 2-3 breaths (about 11 secs) is shown in the middle trace. A second enlargement showing profiles spanning 2-3 cardiac cycles (about 2 secs) is shown in the lower right trace. The manually detected cardiac and respiratory motions are shown with the white dotted lines superimposed on the enlarged traces. This result demonstrates that respiratory and cardiac motion information is contained within the navigator projections with high spatial and temporal resolutions. These data were successfully reconstructed into a cardiac cine set of images shown in FIG. 13.

Figures 13A, 13B:
FIG. 13A shows a cardiac image of a human heart acquired with the subject holding breath.
FIG. 13B shows a cardiac image of the human heart acquired with the subject breathing freely according to some embodiments of the current invention.

FIG. 13A shows a cardiac image of a human heart acquired with the subject holding his breath. FIG. 13B shows a cardiac image of the human heart acquired with the subject breathing freely according to some embodiments of the current invention. The result shows the image quality of a free-breathing patient can be made comparable to that of a patient with breadth-holding without incurring additional hardware or acquisition time, demonstrating the potential of some embodiments of the current invention.

The pulse sequences according to some embodiments of the current invention may benefit from optimization to minimize the imaging TR. To do so, the orientation of the imaging slice (e.g. angulations) should be considered, as should the direction of the readout, the direction of slice selection and the fraction of k-space sampled. Furthermore, it may be possible to shorten TR with slight changes in projection angles as well as with navigator projection resolution.

The acquisition of two echoes could be used for fat-water separation as previously demonstrated by Dixon et al (Dixon, T Simple Proton Spectroscopic Imaging, Radiology 1984; 153:189-194) though for 1.5 T imaging, the echoes should be separated by $0.5*(\omega_{fat}-\omega_{water})$.

The pulse sequences disclosed here according to some embodiments of the current invention are capable of extension into 3D imaging sequences, though the optimization steps required to minimize TRs need to be more involved. Also, multiple navigator directions could be interleaved (e.g. 3 or more different navigator orientations in 3D to robustly map motion). Though only shown with a single navigator direction, TRs with two (or more in 3D) navigator directions could be interleaved. For example, sequences with navigators at +45° and −45° could be interleaved every TR, yielding a temporal resolution of 2*TR for each navigator projection and, more importantly, providing a way of measuring/mapping motion in 2D. The underlying assumption is that examining the motion in more that 1D can only help in the measurement and characterization of the motion.

If the post-processing methods are implemented on the scanner software/hardware platforms, it is possible to use the navigator projection to accept/reject data (e.g., gate) in real-time, or to correct the data based on a measure of motion obtained form the profile (e.g., phase shift). Thus, the pulse sequence according to some embodiments of the current invention may be capable of performing cardiac motion compensation, with the appropriate post-processing of the navigator projection data. These sequences may map both cardiac and respiratory space in a free-breathing acquisition, without the need for external gating. However, respiratory self-navigation can be used in combination with ECG gating and cardiac self-navigation can be used in combination with breath-holds.

The sequence proposed here could be used to reconstruct a complete cardiac-respiratory space. Typically, only the cardiac space is reconstructed (i.e. cine imaging) while compensating for respiratory motion. With this free-breathing self-navigated imaging sequence, a series of images highlighting the cardiac contraction could be reconstructed for every respiratory phase, making it possible to examine the whole cardio-respiratory space.

In addition, the navigator data itself could be included with the data used to reconstruct an image, after appropriate regridding, etc. and should yield an increase in SNR as it is a highly averaged line of k-space.

The pulse sequences disclosed here according to some embodiments of the current invention can also be used in single-phase mode, where other methods (i.e. the standard ECG) is used to gate. Therefore, contrast prepared scans such as delayed enhancement imaging and coronary acquisitions are also possible. High-resolution contrast enhanced images would be very useful for the study of myocardial infarctions, while the ability to generate higher resolution coronary acquisitions is also highly sought-after. For these "single-phase" acquisitions, the appropriate transitions to steady state should be incorporated into the imaging sequence.

Furthermore, an important part of this technique could be a "training" scan, performed upon initiation of the self-navigated acquisition. During this scan, several things could be optimized, including: (1) finding the navigator projection angle that best represented the underlying cardiac and/or respiratory motion patterns (with multiple directions determined for simultaneous cardiac and respiratory self-navigation and for 2D or 3D scans with interleaved directions); (2) finding the navigator projection that minimizes TR; (3) finding the orientation of the readout gradient (readout direction) and slice selection gradient that minimize TR; (4) finding the maximum resolution achievable for the navigator without significant penalties in TR (an important optimization as higher and higher resolution reconstructions are desired).

As discussed, the pulse sequences according to some embodiments of the invention are based on the use of the SSFP imaging pulse sequence. However, they are also applicable for use with fast spin echo and non-steady-state coherent (e.g., standard gradient echo) imaging sequences, albeit with different algorithms for echo combination. However, the SSFP imaging pulse sequence provides the best tradeoff in terms of imaging speed, SNR efficiency and overall resolution.

Though not significantly discussed herein, the pulse sequences disclosed here according to some embodiments of the current invention may be accompanied by diverse methods for motion detection from the navigator projection data. Though some of these methods may be the same as previously published approaches, there are likely to be new developments (yet unknown and undetermined) since no one has demonstrated data with such high temporal and spatial resolution combined.

At the most basic level, the self-navigation pulse sequences according to some embodiments of the current invention can be used to reconstruct cardiac cine images without the need for respiratory compensation in the form of either breath-hold or respiratory navigators.

The imaging pulse sequences according to some embodiments of the current invention have several advantages over standard motion compensation techniques and over other self-navigation approaches. The sequences are capable of scanning a patient in free-breathing, which means that there are no time limits as with breath-holding. The sequences can measure the motion of the heart directly from the heart, making the detection of motion more reliable. Therefore, this self-navigation technique should yield more accurate motion patterns than standard respiratory navigator sequences, which measure the motion of the lung-liver interface and extrapolate (based on population statistics) the motion of the heart. The sequences can acquire navigator projections in very high spatial resolution, since the navigator projection is not constrained in terms of field-of-view (FOV) as is regular imaging. The high-resolution navigator projections can yield extremely accurate motion patterns, again superseding the current capabilities of navigator projections. As mentioned before, no particular image orientation is needed to derive the motion parameters, as long as the organ whose motion is of interest is within the FOV of the image. Also, this new technique does not require a particular orientation of the navigator projection, making it more robust in the face of varied prescribed image orientations. The high sampling rate in space and in time should lead to a better ability to discern the tissue motion, as is necessary to acquire higher resolution images.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A magnetic resonance imaging (MRI) system, comprising:
    a magnetic resonance imaging scanner comprising:
        a main magnet providing a substantially uniform main magnetic field $B_0$ for a subject under observation, said subject represented by a spatial distribution of magnetizations;
        a radio frequency (RF) coil system configured to irradiate a plurality of radio frequency (RF) pulses into a region of interest of said subject and to detect a plurality of RF response signals emitted from said region of interest;
        a gradient coil system configured to provide a perturbation of the main magnetic field $B_0$ using a gradient pulse sequence that causes said RF response signals to encode said spatial distribution of magnetizations in a Fourier domain on a plurality of read-out paths; and
        a controller in communication with said RF coil system and said gradient coil system to synchronously provide said RF coil system with said plurality of RF pulses and said gradient coil system with said gradient pulse sequence, wherein
            said gradient pulse sequence comprises a navigator pulse that causes one of said plurality of RF response signals to encode said spatial distribution of magnetizations in said Fourier domain on a pre-determined navigator path that corresponds to a fixed projection of said region of interest of said subject,
            said pre-determined navigator path is suitable to be in a direction different from directions of said read-out paths, and
            said fixed projection of said subject is capable of tracking a motion of said subject.

2. The MRI system of claim 1, further comprising, a reconstructor to reconstruct a plurality of images representing said region of interest during said motion by combining said plurality of RF response signals.

3. The MRI system of claim 2, wherein at least one of said controller or said reconstructor is computer comprising a processor and a memory.

4. The MRI system of claim 1, further comprising:
    a monitoring device.

5. The MRI system of claim 4, wherein said monitoring device is at least one of a electrocardiogram (ECG) device or a respiration gating device.

6. The MRI system of claim 1, further comprising:
 a intervention device to provide treatment to said region of interest.

7. The MRI system of claim 1, wherein said intervention device is one of a RF ablator, a ultrasound applicator, a laser ablator, a laparoscopic device, or variants thereof.

8. The MRI system of claim 1, wherein said motion is one of a cardiac motion, a respiratory motion, or variations thereof.

* * * * *